US005674505A

United States Patent [19]

Levere et al.

[11] Patent Number: 5,674,505
[45] Date of Patent: Oct. 7, 1997

[54] METHOD FOR TREATING NON-OCULAR EPITHELIAL DISORDERS VIA INCREASING HEME OXYGENASE LEVELS AND/OR DECREASING LEVELS OF ARACHIDONIC ACID DERIVATIVES

[75] Inventors: Richard D. Levere, Armonk; Nadar G. Abraham; Michal L. Schwartzman, both of Elmsford; Michael W. Dunn, New Rochelle, all of N.Y.

[73] Assignee: Hemogen, Inc., Armonk, N.Y.

[21] Appl. No.: 284,354

[22] Filed: Aug. 2, 1994

Related U.S. Application Data

[63] Continuation-in-part of Ser. No. 77,834, Jun. 15, 1993, abandoned, and Ser. No. 990,793, Dec. 10, 1992, abandoned.

[51] Int. Cl.⁶ .................. A61K 7/00; A61K 7/48
[52] U.S. Cl. .................. 424/401; 424/650; 424/434; 424/436; 424/DIG. 13; 424/DIG. 15; 514/863; 514/864
[58] Field of Search .................. 424/401, 650, 424/436, 434, DIG. 13, DIG. 15; 514/251, 863, 864

[56] References Cited

U.S. PATENT DOCUMENTS

| 3,876,765 | 4/1975 | Choay | 424/105 |
| 4,556,560 | 12/1985 | Buckingham | 424/145 |

*Primary Examiner*—Sallie M. Gardner
*Attorney, Agent, or Firm*—Felfe & Lynch

[57] ABSTRACT

Vitamin B12 is used to stimulate heme oxygenase production. In turn, levels of the molecules 12(R)-HETE and 12(R)-DIHETE, which are arachidonic acid derivatives, are reduced. Various topical formulations containing vitamin B12, but no other vitamins, are described.

12 Claims, No Drawings

METHOD FOR TREATING NON-OCULAR EPITHELIAL DISORDERS VIA INCREASING HEME OXYGENASE LEVELS AND/OR DECREASING LEVELS OF ARACHIDONIC ACID DERIVATIVES

This application is a continuation-in-part of application Ser. No. 08/077,834, filed Jun. 15, 1993, now abandoned, and Ser. No. 07/990,793, filed Dec. 10, 1992, now abandoned, both of which are incorporated by reference in their entirety.

FIELD OF THE INVENTION

This invention relates to a method for treating various disorders characterized by either or both of (i) an insufficient amount of heme oxygenase, and (ii) an excess of arachidonic acid metabolites such as, but not being limited to 12(R)-hydroxyeicosatetraenoic acid. It has been found that one may regulate the amounts of these materials via administration of compounds such as $SnCl_2$, other metallic compounds, heme derivatives, and metalloporphyrin ring containing compounds. Cobalt containing metalloporphyrin derivatives such as, but not being limited to, vitamin B12 and its derivatives, are preferred.

BACKGROUND AND PRIOR ART

U.S. Pat. No. 5,102,670, the disclosure of which is incorporated by reference, discloses and claims methods for treating eye disorders. These methodologies involve the administration of agent such as heme derivatives, metals, and vitamin B12, which regulate the following pathway:

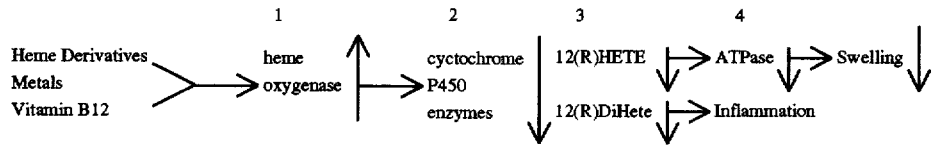

The patent describes how, in the eye, induction of heme oxygenase levels effectively decreased 12(R)-HETE and 12(R)-DIHETE levels.

U.S. patent application Ser. No. 07/990,793 abandoned cited supra, discusses the use of vitamin B12 as an effective agent for treating conditions characterized by excessive cellular exfoliation and/or hyperkeratinization. These conditions which affect the skin and/or scalp, include dandruff (Seborrhea sicca), seborrheic dermatitis, acne vulgaris, rosacea, Herpes zoster, psoriasis and eczema, among others. Additional conditions which exhibit excessive exfoliation include various rashes and allergies, including responses to poison oak, ivy and sumac, allergies, chicken pox, insect bites, athlete's foot, actinic keratitis, contact dermatitis, diaper rash, and all forms of pruritus. Various topical formulations for alleviating these conditions are described. Similarly, conditions which affect the scalp, and treatment via the use of shampoo, e.g., are described. The shampoos contain a primary detergent, such as a fatty alcohol sulfate, an ether sulfate, a sarconisate or some other anionic material, as well as vitamin B12. Additional materials may include aqueous solutions of a soft soap, preservatives, sequestrants, colors, and perfumes.

The conditions are described as being treatable via application of topical formulations and/or shampoos which contain, as their effective ingredient, vitamin B12. Formulations which contain the vitamin in amounts ranging from 0.1 to about 10.0% by weight are described as being preferred, with those containing from about 0.1 weight percent to about 1.0 weight percent vitamin B12 being especially preferred.

The work in this area has been continued. It has now been found that the especially preferred formulations for topical application to skin or scalp may be increased to up to 2.0 by weight, i.e., the preferred range may range from 0.1 to about 2.0 weight percent vitamin B12. It has also been found that compositions containing vitamin B12 may be used as topical formulations for increasing heme oxygenase levels in the skin and other forms of non-ocular epidermis. Such formulations include not only the standard topicals and shampoos, but also formulations such as mouthwashes, gavages, etc., which can be used in formulations for treating oral epidermic cells, aerosols for treating nasal tissue, suppositories, and so forth. The invention is described in greater detail in the disclosure which follows.

These formulations are exemplary of the formulations which are useful in this invention, which concerns the treatment of conditions, especially epidermal disorders, via administration of a composition containing at least one agent which stimulates production of heme oxygenase, and/or inhibits production of 12(R)-HETE. Among the compounds useful in these therapies are metal ion containing compounds, especially compounds containing Cr, Mn, Fe, Ni, Cu, Zn, Au, Hg, Pb, Cd, Sn, Pt and Sb, with $SnCl_2$ being especially preferred, heme derivatives, metalloporphyrin ring containing compounds, such as those which contain cobalt. Vitamin B12 is one example of such a compound.

The active ingredients are administered in formulations, which contain anywhere from 0.01% by weight to 10.0% by weight of the active compound or compounds. More preferably, the amount is from 0.1 to 2.0 percent by weight, and 0.1 to 1.0 percent by weight compositions and/or formulations may also be used.

SUMMARY OF THE INVENTION

The invention relates to methods for increasing heme oxygenase levels or reduction of 12(R)-HETE levels in non-ocular epidermal tissue via administration of a heme oxygenase increasing or 12(H)-HETE decreasing effective amount of a compound of the group described, supra to a subject in need thereof. In particular, the method involves treating skin in the manner indicated, such as oral and nasal mucosa. The invention also involves compositions useful in the treatment of such conditions, where the compositions include sufficient active ingredient to stimulate increased production of heme oxygenase levels or to decrease 12(R)-HETE levels, where the compositions do not include any other vitamins or vitamin derivatives other than vitamin B12, nor do they contain, e.g., tannic compounds. Vitamin derivatives, as used herein refers to any compound based upon a vitamin produced via chemical reaction with another compound. "Arachidonic acid derivative" means a compound which is a metabolite of arachidonic acid and may have, e.g., an eicosatetraenoic acid based structure or "backbone" 12(R)-HETE and 12(R)-DiHete are exemplary, but are by no means exhaustive. Examples which are illustrative of vitamin derivatives, but are not exhaustive of these, can be found in, e.g., U.S. Pat. No. 5,053,222 to Takasu, et al., which discloses diesters of phosphoric acid and tocopherol (vitamin E). Such derivatives, and others of this type, are not included in the invention described herein. The conditions which can be so treated include those where non necrotizing thermal injury has occurred. Such conditions include sunburn and other conditions caused by excessive exposure to ultraviolet irradiation, actinic keratitis, burns caused by, e.g., exposure to hot or boiling water or hot metal surfaces, and so forth. Additionally, conditions characterized by skin eruptions and/or inflammation, including herpes simplex and herpes zoster, psoriasis, acne, and so forth, may also be treated in the thus described manner.

Further conditions treatable via the described methodology are primary burns, chapped skin and lips, athlete's foot, minor abrasions linked to inflammation, abrasions from minor skin injuries such as shaving abrasions, and so forth. Also treatable are ulcerations of the mucus membranes, such as oral, nasal and rectal mucosa, oral conditions such as gingivitis, and so forth. Relates conditions will be known to the skilled artisan, and are not set forth here.

DETAILED DESCRIPTION OF PREFERRED EMBODIMENTS

The invention embraces formulation useful in the treatment of conditions where increasing the level of heme oxygenase and/or decreasing the level of 12R(HETE) is desirable. The formulations are characterized by an amount of the compounds described herein sufficient to stimulate increased production of the enzyme or to decrease 12(R)-HETE levels, and do not contain any other vitamins or vitamin derivatives. The compositions may include other materials, as described infra, including a pharmacologically acceptable carrier.

In its broadest embodiment, the compositions of the invention may include merely an amount of the active ingredient sufficient to stimulate heme oxygenase and a pharmaceutically acceptable carrier. In practice, such formulations are not preferred as much as, e.g., shampoos, hand cremes, skin cremes, salves, balms, mouth washes, gavages, suppositories and so forth. Particularly preferred are shampoos, including liquids, lotions, gels, emulsions, powders, creme rinses, and other standard formulations of shampoos. They can also be formulated in compositions such as dishwashing liquids for treatment of "chapped" or "dishpan" hands, lip balms, lipsticks, other cosmetics, and so forth. In one desirable embodiment, the formulations are prepared so as to be "hypoallergenic".

A standard shampoo, in accordance with the invention may include, e.g., the following formulation:

| Ingredient | wt % | Function |
| --- | --- | --- |
| sodium lauryl sulfate (30%) | 40.0 | cleansing agent |
| lauramide DEA | 4.0 | Foam stabilizer |
| disodium EDTA | 0.1 | sequestering agent |
| formaldehyde | 0.04 | preservative |
| FD + C Blue No. 1 | 0.001 | color |
| FD + C Yellow No. 1 | 0.004 | color |
| deionized/distilled water | 55.36 | solvent |

The foregoing is a clear liquid shampoo. An alternative formulation is:

| Ingredient | wt % | Function |
| --- | --- | --- |
| TEA lauryl sulfate (40%) | 20.0 | cleanser |
| Sodium lauryl sulfate (29%) | 20.0 | cleanser |
| cocoamide DEA | 5.0 | Foam stabilizer |
| glycol stearate | 1.0 | opacifying, pearlescent agent |
| disodium EDTA | 0.1 | sequestering agent |
| methylparaben | 0.1 | preservative |
| propylparaben | 0.01 | preservative |
| fragrance | 0.5 | fragrance |
| deionized/distilled water | 53.29 | solvent |

This formulation is a pearlescent or opaque liquid.

Different formulations may be used, and indeed, any of the standard shampoos available over the counter, as well as those available only by prescription may be used as carriers for the active ingredient, e.g., vitamin B12 or some other cobalt containing metalloporphyrin ring compound, other metalloporphyrin containing compounds such as cadmium protoporphyrin, cobalt protoporphyrin, and lead protoporphyrin heme derivatives, such as iron porphyrin or heme arginate, metal ion containing compound, and so forth. When the formulation is to be applied to skin as compared to scalp, any of the standard skin cremes, lotions, gels, liquids, sprays, etc., may be modified to incorporate vitamin B12 therein. When used as a mouthwash, standard mouthwash formulations may be adapted for the invention by incorporating metalloporphyrin compounds especially those containing cobalt, such as vitamin B12 therein.

"Vitamin B12", as used herein, refers to all forms of the molecule, as well as to its salts. The fundamental portion of the molecule for purposes of the invention is the coordination compound formed by cobalt and its porphyrin ring. It is to be understood that the vitamin may be treated to render it more soluble in the particular carrier of choice, via, e.g., reacting it to form an acid addition salt, or in any other way which does not impact the fundamental portion of the molecule described supra.

The invention also encompasses therapeutic methods for treating the conditions discussed herein by administering an amount of the active compound, such as a cobalt containing, metalloporphyrin ring compound (e.g., vitamin B12) sufficient to stimulate heme oxygenase production to the site of the condition. The dose will vary, depending upon the condition, the patent and the severity of the condition, but a general range may be to use a composition containing anywhere from 0.01 to 10.0% by weight of active compound. A particular preferred range runs from about 0.1 weight percent to about 2.0% weight percent, relative to the composition.

The efficacy of the compositions in accordance with this invention is shown in the following examples.

EXAMPLE 1

A standard shampoo ("IVORY"), contains water, ammonium laureth sulfate, ammonium lauryl sulfate, glycol distearate, cocoamide dea, dimethicone, citric acid, sodium hydroxide, fragrance, EDTA, xylene sulfonate, ammonium chloride, methyl chloroisothiazolinone, and methyl isothiazolinone. This "over the counter" composition was modified by including vitamin B12 (1 mg per 100 ml of shampoo, i.e., 1% by weight). The shampoos were provided to subjects having severe dandruff problems. Subjects were shampooed once per day with the formulations, and after 2–4 days, scurf was absent. The shampoos was applied for a period of 10 days, during which time no dandruff was evident.

In a control, the same subjects were then provided with the standard shampoo without vitamin B12, and used this for seven days. Dandruff reappeared. Upon reapplication of the vitamin B12 containing formulations, however, the dandruff was again alleviated.

EXAMPLE 2

In a follow-up experiment, a standard shampoo was modified by incorporating 2% by weight of vitamin B12 therein. Ten subjects suffering from dandruff were provided with the formulation, and were instructed to use it in the same manner as were the subjects in the first example. The subjects were monitored over a two week period. In all cases, dandruff was eliminated.

EXAMPLE 3

The results secured with vitamin B12 on dandruff suggested that experiments be extended to studies on skin. An in vitro skin fibroblast model was used, which is predictive of efficacy on skin in vivo.

Cell line CCD-860SK is a human skin fibroblast cell line which is publicly available from the American Type Culture Collection. Cell cultures of this line were propagated in Iscove's modified Dulbecco's medium supplemented with 10% fetal bovine system. Following propagation, they were grown in 175 cm² Falcon tissue culture flasks, using Iscove's modified Dulbecco's medium, supplemented with 10% (v/v) heat inactivated fetal bovine serum, 50 U penicillin/ml, 50 ug streptomycin/ml, and 2 mM glutamine. The cells were then seeded into culture flasks at a concentration of $1 \times 10^5$ cells/ml, and incubated at 37° C. in a humidified 5% $CO_2$/95% air chamber. After three days, old media were removed, and replaced with fresh media. Controls received no test substance, while others received one of the following: heme (5–10 μM), vitamin B12 (10–100 μM), zinc 2,4 bis glycol (10 μM), tin protoporphyrin (Sn PP; 5–10 μM), dexamethasone (50 ug/ml), cyclohexamide (1 ug/ml), actinomycin D (1 ug/ml), zinc protoporphyrin (ZnPP; 10 μμ), poly I:C (50 ug/ml), endotoxin (50 ug/ml), $SnCl_2$ (1–10 μM), and $CoCl_2$ (1–10 μM).

After two hours, cells were collected, and tested for heme oxygenase activity using two methods: enzyme activity, and total message RNA.

To measure total enzyme activity, microsomes were prepared as described by Tenhunen et al., J. Biol. Chem. 244:6388–6394 (1969), incorporated by reference herein. The activity of microsomal heme oxygenase was then determined, using 0.5–1 mg protein in an incubation medium as described by Tenhunen et al., supra. Total protein was then determined using the classic method of Lowry et al., J. Biol. Chem. 193:265–175 (1951), using bovine serum albumin as standard.

The results for vitamin B12 and $SnCl_2$ are presented in Table 1.

TABLE 1

Effect of vitamin $B_{12}$ and $SnCl_2$ on CCD-860 skin fibroblast cell heme oxygenase activity

| | Heme oxygenase pmol bilirubin/mg/hr |
|---|---|
| Experiment I | |
| Control | 294 ± 18 |
| $SnCl_2$ (100 μM) | 802 ± 49* |

TABLE 1-continued

Effect of vitamin $B_{12}$ and $SnCl_2$ on CCD-860 skin fibroblast cell heme oxygenase activity

| | Heme oxygenase pmol bilirubin/mg/hr |
|---|---|
| Vitamin $B_{12}$ (10 μM) | 297 ± 12 |
| Vitamin $B_{12}$ (100 μM) | 462 ± 34* |

Results are expressed as the mean ± SD. *p < .001 vs. control.

EXAMPLE 4

The second half of the experiment discussed in example 3 involved the determination of RNA message for heme oxygenase. To do this, a probe was prepared. The probe was the 833 base pair ECORI/HindIII fragment prepared from vector pRHOL. This vector is a plasmid which contains full length cDNA for heme oxygenase, as described by Shibahara et al., J. Biol. Chem. 262: 12889–12892 (1987), which is incorporated by reference in its entirety.

The probes was obtained following restriction endonuclease treatment, via electrophoresis in low temperature gelling agarose, followed by excision of the band described by Abraham et al., Int. J. Cell Cloning 9: 185–210 (1991). The DNA was labelled with [α³²P]dCTP using a standard multiprime labelling kit, achieving specific activity of 1–2 cpm/ug. In the experiments which follow, it was used at a concentration of $10^6$ cpm/ml relative to the hybridization mixture.

The thus prepared probe was used in Northern Blot analysis of total cellular RNA. A minimum of $5 \times 10^7$ cells per sample were pelleted, using the classic method of Chirgwin et al., Biochem. 18: 5294–5299 (1977). Ten microgram quantities of the fibroblast total RNA were denatured and size separated via electrophoresis at 100 v for 2.5 hours in 1.5% (w/v) agarose formaldehyde, followed by blotting to nitrocellulose membranes. The blotted RNA was hybridized with the labelled probes discussed supra, following Shibahara et al, supra. Post hybridization washes were carried out at 45° C. in 1×SSC (150 mM NaCl/15 mM Na citrate), and 0.1% SDS. Binding was determined using standard autoradiography.

The results are depicted in FIG. 1. Lane 1 is a control. Lane 2 used vitamin B12 at 10 μM. The third lane shows results from vitamin B12 at 100 μM, whereas lane 4 shows the results where $SnCl_2$ was used at 100 uM. Finally, lane 5 shows the results using 10 uM of heme. It will be seen that vitamin B12 clearly increased the amount of message. This correlates to the results supra, showing that enzyme activity increased, thus indicating increased levels of heme oxygenase in the target.

The foregoing demonstrates the efficacy of the compositions in accordance with this invention. It will be seen that many skin and scalp directed compositions are known, and incorporation of the active ingredient therein does not present any difficulties. Thus, the invention as described supra is well within the hands of the skilled artisan, once the key feature, e.g., the use of vitamin B12, or other metalloporphyrin compounds is provided.

The invention involves formulations which are compositions containing sufficient vitamin B12 to stimulate production of heme oxygenase or to inhibit arachidonic acid derivatives, such as 12(R)-HETE, when applied to the intended site. These compositions are designed for topical use, such as the skin cremes, lotions, shampoos, mouthwashes, nasal aerosols, suppositories and so forth described supra. As indicated, the compositions preferably contain anywhere from about 0.01% to about 10.0% by weight of active ingredient, in combination with other ingredients. Such formulations should not contain any other vitamins or vitamin derivatives.

In addition, the invention involves methods for treating disorders of the epidermis where increased levels of heme oxygenase or decreased levels of arachidonic acid derivatives, such as 12(R)-HETE are desirable. These methods involve applying to the site of the condition an amount of vitamin B12 sufficient to provoke and or to stimulate increased levels of heme oxygenase in the epidermis. Specifically excluded from treatment in this invention is treatment of the eye. Disorders contemplated for treatment include those described in the Summary of the Invention, supra, and for that reason are not reiterated here.

Other aspects of the invention will be clear to the skilled artisan and are not repeated here.

It will be understood that the specification and examples are illustrative but not limitative of the present invention and that other embodiments within the spirit and scope of the invention will suggest themselves to those skilled in the art.

We claim:

1. A method for increasing levels of heme oxygenase and decreasing levels of arachidonic acid in non-ocular epidermal tissue, comprising applying to non-ocular epidermal tissue of a subject in need thereof an amount of $SnCl_2$ sufficient to increase levels of heme oxygenase and decrease levels of arachidonic acid in said non-ocular tissue.

2. The method of claim 1, wherein said arachidonic acid is 12(R)-hydroxyeicosatetraenoic acid.

3. The method of claim 1, wherein said non-ocular epithermis is the scalp.

4. The method of claim 1, wherein said non-ocular epithermis is the skin.

5. The method of claim 1, wherein said non-ocular epithermis is the lips.

6. The method of claim 1, wherein said $SnCl_2$ is administered in the form of a composition containing said $SnCl_2$ in an amount ranging from about 0.1% to about 2.0% by weight.

7. The method of claim 1, wherein said $SnCl_2$ is administered in the form of a composition containing said $SnCl_2$ in an amount ranging from about 0.1% to about 1.0% by weight.

8. The method of claim 6, wherein said composition is a shampoo and is administered to the scalp.

9. The method of claim 6, wherein said composition is a lotion or skin creme.

10. The method of claim 6, wherein said compositions is a mouthwash or gavage and is administered orally.

11. The method of claim 6, wherein said composition is a suppository.

12. The method of claim 6, wherein said composition is a nasal aerosol, and is administered nasally.

* * * * *